US006960378B1

(12) United States Patent
Siegel et al.

(10) Patent No.: US 6,960,378 B1

(45) Date of Patent: Nov. 1, 2005

(54) TUBULAR MICROSTRUCTURES VIA CONTROLLED NANOPARTICLE ASSEMBLY

(75) Inventors: Richard W. Siegel, Menands, NY (US); Linda S. Schadler Feist, Clifton Park, NY (US); Dongling Ma, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 37 days.

(21) Appl. No.: 10/608,892

(22) Filed: Jun. 27, 2003

Related U.S. Application Data

(60) Provisional application No. 60/392,292, filed on Jun. 27, 2002.

(51) Int. Cl.[7] ........................................ A61M 5/00

(52) U.S. Cl. ...................... 428/36.9; 128/898; 216/75; 604/191

(58) Field of Search ...................... 428/36.9; 128/898; 216/75; 604/191

(56) References Cited

U.S. PATENT DOCUMENTS

| | | | | |
|---|---|---|---|---|
| 6,146,663 | A | 11/2000 | Bissery et al. | 424/489 |
| 6,334,856 | B1 * | 1/2002 | Allen et al. | 604/191 |
| 6,413,489 | B1 | 7/2002 | Ying et al. | 423/600 |
| 6,420,293 | B1 * | 7/2002 | Chang et al. | 501/95.2 |
| 6,462,100 | B1 | 10/2002 | Thunhorst et al. | 521/53 |
| 6,696,565 | B2 * | 2/2004 | Fenniri | 544/244 |

FOREIGN PATENT DOCUMENTS

KR 2002040644 A * 5/2002 ............ B01J 35/02

OTHER PUBLICATIONS

Rundgren et al., *Ceramic Industry*, 2003: Apr.: pp. 40-44.

* cited by examiner

*Primary Examiner*—Sandra Nolan Rayford
(74) *Attorney, Agent, or Firm*—Heslin Rothenburg Farley & Mesiti P.C.

(57) ABSTRACT

A process for producing microtubes from nanoparticles includes forming a dispersion of the nanoparticles in a liquid phase and freeze-drying the dispersion to produce microtubes. The nanoparticles have surface functionality capable of self-bonding and bonding with the liquid phase during freeze-drying, particularly surface hydroxy functionality.

16 Claims, 2 Drawing Sheets

TUBULAR MICROSTRUCTURES VIA CONTROLLED NANOPARTICLE ASSEMBLY

CROSS-REFERENCE TO RELATED APPLICATIONS

This application is a non-provisional of, and claims priority from, U.S. Ser. No. 60/392,292, filed Jun. 27, 2002 now abandoned, the entire disclosure of which is incorporated herein by reference.

FIELD OF THE INVENTION

The invention relates to a freeze-drying process for producing tubular microstructures from nanoparticles, and the microtubes produced thereby.

BACKGROUND OF THE INVENTION

Owing to various novel properties of nanoparticles, (see, for example, R. W. Siegel, E. Hu, and M. Roco (eds.), *Nanostructure Science and Technology* 1999) it is of increasing interest to use them as building blocks for well-defined structures that have practical applications. However, their assembly is a challenging task. Methods based on surface functionalization, and/or template patterning have been used for this purpose, but both of these processes can be rather complicated. Therefore, there is a continuing need for a simple method for synthesizing high aspect ratio microstructures constituted of nanoparticle building blocks.

SUMMARY OF THE INVENTION

It has been unexpectedly discovered that a process based on freeze-drying a dispersion of nanoparticles can produce tubular microstructures, herein termed "microtubes". In the process, nanoparticles having surface functionality capable of self-bonding are dispersed in a liquid capable of bonding with the surface functionality and the dispersion is freeze-dried. This process for the assembly of nanoparticles has great significance and beauty because of its simplicity, and also because of its ability to enable the self-organization of even rather weakly interacting nanoparticles into lower energy end-capped tubular structures. This powerful method for the self-organization of even weakly interacting nanoparticles can be easily scaled up to produce larger material quantities, due to its general applicability.

In the context of the present invention, 'nanoparticle' is defined as a particulate material having an average particle or grain size between 1 and 100 nanometers. Similarly, a 'microstructure' or 'microtube' is defined as a structure having at least one dimension such as length or diameter in the micron range, that is, greater than about 1 $\mu$m.

Accordingly, in one aspect, the present invention relates to a process for producing microtubes from nanoparticles. The process includes forming a dispersion of the nanoparticles in a liquid phase and freeze-drying the dispersion to produce microtubes. The nanoparticles have surface functionality capable of self-bonding and bonding with the liquid phase during freeze-drying, particularly surface hydroxy functionality.

In another aspect, the invention relates to tubular microstructures derived from nanoparticles having surface functionality capable of self-bonding. The surface functionality is preferably hydroxy functionality, and the nanoparticles are preferably composed of metal oxide.

The process appears to be driven by capillarity during freeze-drying, which makes it quite general in terms of its easy applicability to a wide variety of nanoparticle-assembled materials.

DETAILED DESCRIPTION OF THE INVENTION

Figure 1A:
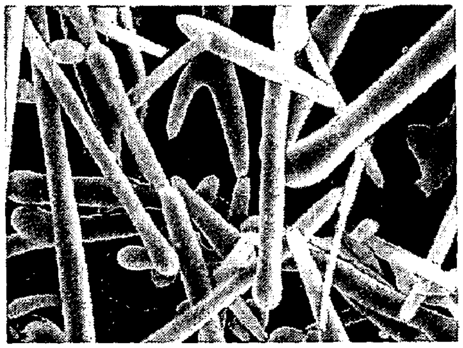
FIGS. 1A–1C are FESEM images showing the end-capped $TiO_2$ microtubes, an individual microtube with its constituent nanoparticles, and the hollow nature of the microtubes, represented by Bar: 1 $\mu$m in a; 100 nm in b and c.

The present invention relates to tubular microstructures resulting from self-assembly of nanoparticles into hollow cylindrical structures. In the context of the present invention, these tubular microstructures are also termed "microtubes". The term "microtube," as used herein, refers to a particulate material having a cylindrical or tubular configuration. The average diameter of the microtubes is approximately 1 $\mu$m, and may range from 0.01 to 100 $\mu$m. The microtubes have a very high aspect ratio, that is, ratio of length to diameter, ranging from 10 to 1,000. Tube wall thickness typically ranges from about 20 nm to about 100 nm, when nanoparticles having an average particle size of 18 nm are used as starting materials. This range corresponds to the diameter of a single nanoparticle at the low end and the diameter of multiple nanoparticles at the high end. The ranges are exemplary for this particle size, and vary according to the particle size of the particular nanoparticles used. In addition, dimensions of the microtubes may be varied by varying parameters of the process used for their synthesis. The microtubes may have an open end or be closed with a rounded end cap, also composed of self-assembled nanoparticles. FIG. 1 depicts a collection of titanium dioxide microtubes formed from a dispersion of titanium dioxide nanoparticles in water. Most tubes have a diameter of about 1 $\mu$m and lengths range from several to over 100 $\mu$m.

Nanoparticles that may be used as building blocks for the microtubes of the present invention have surface functionality that is capable of self-bonding, that is, chemical group(s) that form(s) bonds with the same type of group. One example of self-bonding functionality is a hydroxy group, which forms hydrogen bonds with other hydroxy groups. The functionality should also be capable of bonding or at least interacting strongly with a liquid phase during self-assembly from a dispersion of the nanoparticles in that liquid phase, as for example, hydroxy groups from hydrogen bonds with water, and organic liquids containing groups with polar oxygen atoms. Examples of nanoparticles having surface hydroxy groups are titanium dioxide nanoparticles, aluminum oxide nanoparticles, and zinc oxide nanoparticles. Interaction with an aqueous phase is believed to be an important factor in self-assembly of metal oxide nanoparticles to form microtubes.

Nanoparticles having self-bonding functionality on their surface and found to be useful as starting materials for fabricating the microtubes of the present invention may be composed of metals or metal oxides, nitrides, carbides, carbonitrides, oxynitrides and oxycarbonitrides, or mixtures thereof. Any metal that may be appropriately functionalized may be used, including aluminum, titanium, and zinc. In particular, the nanoparticles may be composed of metal oxides. Examples of metal oxides useful for the nanoparticles are magnesium oxide, yttrium oxide, cerium oxide, alumina, titania, and zirconia. Other compositions that may be used include metal nitrides, metal carbides, metal carbonitrides, metal oxynitrides, metal oxycarbonitrides, or mixtures thereof. The metal of these compounds may be aluminum, titanium, zirconium, magnesium, yttrium, or cerium; in particular, the metal may be aluminum, zinc or titanium. Non-metals such as calcium, silicon and germanium, and particularly silicon, may be useful as oxides, nitrides, carbides, carbonitrides, oxynitrides and oxycarbonitrides for use in the nanoparticles. Examples of non-metal compositions are silicon carbide and silicon nitride. Semimetals such as bismuth and beryllium may also be useful as oxides, nitrides, carbides, carbonitrides, oxynitrides and oxycarbonitrides. Examples of non-metal oxides are bismuth oxide and beryllium oxide. Mixed compounds such as SiAlON, calcium aluminate, mullite ($Al_2O_3$' $SiO_2$), and spinel (MgO $Al_2O_3$) may be used. Carbon particles having surface self-bonding functionality may also be used in the practice of the invention. Composite nanoparticles having a core-shell morphology may also be used. An interesting example of this is a nanoparticles having a core composed of a magnetic metal such as iron surrounded with a shell composed of a hydroxy-functional metal oxide.

Nanoparticles of any size, that is, ranging from about 1 nm to about 100 nm, may be to form microtubes according to the present invention. Particle size preferably ranges from about 10 nm to about 50 nm, and even more preferably from about 10 to about 30 nm.

Particle size distribution is typically narrow. A narrow particle size distribution is defined as one in which greater than 90% of the particles have a particle size in the range of 0.2–2 times the mean particle size. Preferably, greater than 95% of the particles have a particle size in this range, and more preferably greater than 99%. Another way to define a particle size distribution is in terms of the mean particle size and the width of the distribution; this method is used in the nanoparticle industry. The relationship between the width of the distribution curve at one half of the maximum value (full width-half max or FWHM) and mean particle size is used as a measure of broadness or narrowness of the distribution. For example, a distribution having a FWHM value that is greater than the mean particle size is considered relatively broad. Specifically, a narrow particle size distribution is defined in terms of FWHM as a distribution in which the FWHM of the distribution curve is equal to the difference between the mean particle size plus 40% of the mean and the mean minus 40% of the mean. (This may be simplified to two times 40% of the mean, or 80% of the mean. Using this simplified formula, the FWHM is less than or equal to 80% of the mean.) Preferably, the FWHM is less than or equal to the difference between the mean plus 30% and the mean minus 30% (60% of the mean.) More preferably, the FWHM is less than or equal to the difference between the mean plus 20% and the mean minus 20% (40% of the mean).

Nanoparticles useful in the present invention are typically equiaxed, such that their shape is quasi-spherical. The long axis of a particle is defined as the longest axis through a particle, and the short axis means the shortest axis through a particle. The long axis of the nanoparticles for use in the present invention is approximately equal to the short axis, resulting in a particle shape which is quasi-spherical. For at least 90% of the nanoparticles, the ratio of the length of the short axis to that of the long axis is at least 0.1, preferably 0.4, and more preferably 0.8.

Further, the surface of a nanoparticle utilized in the present invention is typically chemically clean, that is, uncontaminated by residues from chemicals used in the synthetic process. Methods that produce nanoparticles from a gas phase, such as a gas condensation process, such as that described in U.S. Pat. Nos. 5,128,081 and 5,320,800, the contents of which are incorporated herein by reference, typically yield a clean surface. Nanoparticles made by wet chemical methods are often contaminated by residues from chemicals used in the process; these particles may be subject to a post-production clean-up process to yield a chemically clean surface. For example, many processes for the production of titanium dioxide particles involve the oxidation of $TiCl_4$ to $TiO_2$. The surface of particles produced by this process contains residual chloride ions from the $TICl_4$. These residues may be removed by chemical cleaning processes, if desired. Nanoparticles produced by a gas condensation process are not contaminated by process residues, because no solvents, reagents or intermediates are used. Therefore, nanoparticles for use in the present invention are preferably prepared by a gas condensation process.

A gas condensation process for the preparation of nanoparticles typically involves evaporation of a metal precursor material from which the nanoparticles will be synthesized at gas pressures of less than one or equal to one atmosphere. The evaporated metal condenses into small particles in the gas atmosphere and the resulting nanoparticles are collected on a surface within the reactor. Any metal or metal compound capable of being volatilized may be used in this process. Exemplary metals are titanium, copper, silver, gold, platinum, and palladium. The metal nanoparticles may be further subjected to a reactive gas atmosphere to form oxides, nitrides, carbides, sulfides, fluorides, and chlorides. Exemplary metal oxide nanoparticles are those composed of aluminum oxide, antimony tin oxide, cerium oxide, copper oxide, indium oxide, indium tin oxide, iron oxide, tin oxide, titanium dioxide, yttrium oxide, zinc oxide, barium oxide, calcium oxide, chromium oxide, magnesium oxide, manganese oxide, molybdenum oxide, neodymium oxide, and strontium oxide. Metal titanate and metal silicate nanoparticles including, for example, strontium titanate, barium titanate, barium strontium titanate, and zirconium silicate may also be used. Titanium dioxide nanoparticles of varying particle size, synthesized by a gas condensation process, are commercially available from Nanophase Technologies Corporation. Nanophase Technologies also manufactures the metal, metal oxide, metal titanate and metal silicate nanoparticles listed above.

Nanoparticles used in the present invention are crystalline materials, and are referred to as nanocrystalline. Each of these particles is composed of a single grain, that is, a single crystal consisting of atoms arranged in an orderly pattern. Nanocrystalline materials have grains containing thousands to tens-of thousands of atoms as compared to millions or trillions of atoms in the grains of conventional particles, and have a significantly higher percentage of atoms present on the surface of the particle.

The present invention also relates to a process for producing tubular microstructures or microtubes. Microtubes are produced by forming a dispersion of nanoparticles in a liquid phase and freeze-drying the dispersion. The nanoparticles have surface functionality capable of self-bonding and bonding with the liquid phase during freeze-drying. In a preferred embodiment, the nanoparticles have hydroxy groups or functionality on their surface, and the liquid phase is a hydrogen-bonding liquid, preferably an aqueous liquid. It is believed that hydrogen bonding between the hydroxy groups on the surface and between these groups and hydrogen-bonding groups in the liquid phase facilitates self-assembly of the nanoparticles into microtubes. Where the nanoparticles are hydroxy-functional, and the liquid phase is a hydrogen-bonding liquid, the concentration of nanoparticles in the liquid may range from about 0.0025 g/ml to about 0.0625 g/ml. Preferred nanoparticles having hydroxy functionality are metal oxide nanoparticles, particularly titanium dioxide, aluminum oxide (alumina) or zinc oxide. A preferred hydrogen-bonding liquid is water; other hydrogen-bonding liquids that may be used are alcohols, or combinations of water with other hydrogen-bonding liquids, such as a combination of water with one or more alcohols. It should be noted that any hydrogen-bonding liquids used in the process of the present invention should be suitable for freeze-drying, that is, having a suitable freezing point, and be removable in the frozen state by sublimation.

The dispersion may contain dissolved or dispersed components other than the nanoparticles, but these should not interfere with how the nanoparticles and the liquid phase interact to produce the microtubes. For example, surfactants may be included if interactions are not disrupted. Where the liquid phase is water, pH of the dispersion may be adjusted from the starting pH, but not to a pH value where interactions are interfered with. For example, microtubes may be produced from dispersions where the nanoparticles are composed of titanium dioxide and have hydroxy groups on the surface at an unadjusted pH of about 2.3; the pH of the dispersion may range from 1.8 to 2.8, while still yielding microtubes on freeze-drying, but at a pH of 1.7 or lower, or 2.9 or higher, no microtubes were produced. Therefore, preferred ranges for pH are, in order of preference, 1.9 to 2.7, 2.0 to 2.6, 2.1 to 2.5, and 2.2 to 2.4.

Commercially available nanoparticles typically contain a small number of particles having a size in the micron range. It is not necessary to separate these relatively large particles from the nanoparticle starting material in order to obtain microtubes. However, if desired, the separation may be effected by known techniques for removing large particles from a dispersion, such as centrifugation. Therefore, in order to narrow the particle size distribution of the nanoparticles, and particularly, to remove particles having a relatively large particle size, especially those in the micron range, it may be desirable to centrifuge the dispersion and freeze-drying the only the supernatant portion. Centrifuging times and speeds are not critical, and this technique for narrowing particle size distribution is well known. Suitable centrifuging parameters may be readily determined by examination of the particle size distribution at various times and speeds.

The present invention is useful in a number of applications ranging from structural reinforcements in polymer matrices to drug delivery vehicles.

EXAMPLES

Example 1

$TiO_2$ nanoparticles with an average diameter of 36 nm (Nanophase Technologies Corporation) were used without further purification or drying. First, 5 g of nanoparticles were dispersed in 90 ml of distilled water by sonication. The slurry was then centrifuged at 10,000 revolutions per minute for 10 minutes to refine the particle size distribution. The dilute suspension after centrifuging was decanted and left in a glass bottle for further deposition of bigger particles for at least 10 hours. The top thin suspension was then decanted again and frozen in liquid nitrogen for 0.5 hr. Finally the frozen mixture was placed in a freeze drier for the formation of tubular $TiO_2$ material.

Example 2

Figure 1B:
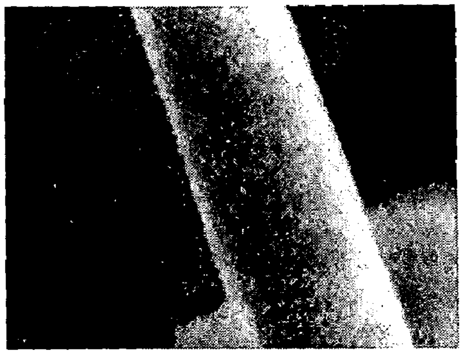
Figure 1C:
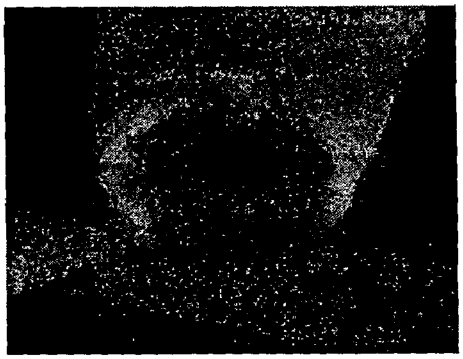

Field emission scanning electron microscopy (FESEM) and transmission electron microscopy were used to observe the arrangement of $TiO_2$ nanoparticles in the self-assembled structure. FIGS. 1A–1C show FESEM images of the synthesized tubular material at different magnifications after one day of freeze-drying. Tubes have a diameter of about 1 $\mu$m with lengths ranging from several to over 100 $\mu$m were observed, along on some sheets. The low-energy closed end-cap morphology of the microtubes is seen clearly in FIG. 1A. The outer surface of the tube appears quite smooth, but at higher magnification (FIG. 1B), the constituent nanoparticles are clearly seen. The hollow nature of the tubes can be seen in FIG. 1C. Our FESEM observations indicate that the tube wall thickness varies from several tens to over 100 nm.

Figure 2:
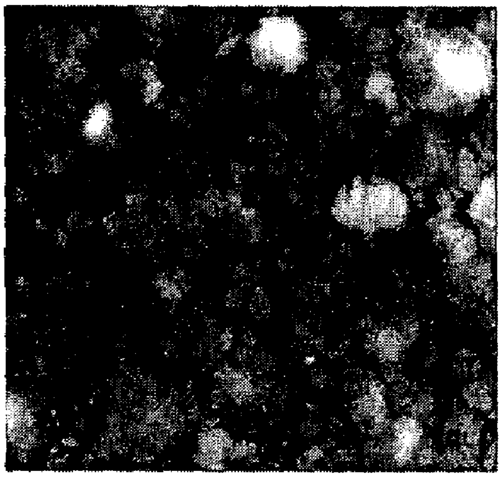
FIG. 2 is a transmission electron microscopy image showing the $TiO_2$ nanoparticle arrangement in a sheet.

FIG. 2 shows the arrangement and size distribution of nanoparticles in the sheet structures as seen by transmission electron microscopy. The largest particle diameter found is 60 nm and most are smaller than 30 nm, similar to those observed in the tubes, and also similar to those observed after centrifuging, but before freeze-drying.

With an increase of freeze-drying time, the relative amount of tubes in the resulting structures increases, which may indicate a structure transition from sheets to lower-energy tubes with time. In fact, FESEM images (not shown) depict sheet structures along with partially formed tube structures, some of them apparently growing out of the sheets. Sheets with many holes are also observed, and these holes have diameters comparable to the tube diameters. When the pH value of the suspension changed by 0.5, either increasing or decreasing, all regular tube structures disappeared and mostly sheets were observed.

Example 3

X-ray diffraction measurements of the as-received $TiO_2$ nanoparticles and the tubular $TiO_2$ formed during freeze-drying indicated no changes in crystal structure. The chemical nature of the $TiO_2$ tubes was confirmed by selected area energy dispersive X-ray spectroscopy and Raman spectroscopy. The micrographics indicate that the microtubes are composed of Ti and O ignoring some undetectable light elements and background signals. Strong $K_\alpha$ and $K_\beta$ signals from Ti were seen at 4.51 and 4.93 KeV respectively. Because the $L_\alpha$ peak from Ti and the $K_\alpha$ peak from O are so close that they are superimposed, a quantitative Ti/O ratio analysis has not been performed due to the difficulty of accurately splitting the $K_\alpha$ peak at 0.523 KeV and the $L_\alpha$ Ti peak at 0.452 KeV. However, the approximate Ti/O ratio can be estimated from the ratio of the heights of the O peak at 0.523 KeV and the Ti peak at 4.51 KeV. This ratio was different in the two samples that were examined.

While a quantitative Ti/O ratio analysis was not performed on individual tubes using selected area energy dispersive X-ray spectroscopy, the average composition of the tubular $TiO_2$ was determined by Raman spectroscopy and compared with that of the as-received $TiO_2$ (see FIG. 4). All four bands are attributed to the anatase phase of $TiO_2$, matching our X-ray diffraction results. According to Parker and Siegel (Applied Physics Letters, 79, 3702 (2001)), a change of the Ti/O ratio causes Raman band shifting and changes of peak width. By considering only the intense band at 145 $cm^{-1}$, and comparing our results on band position and width with those of Parker and Siegel, it was found that the average Ti/O ratio (in the range of 1.98–2.0) was the same for both as-received nanoparticles and the tubular $TiO_2$.

From crystal structure and chemical composition analyses, along with electron microscopy observations, it was concluded that the formation of the observed $TiO_2$ microtubes occurs through the physical rearrangement or self-organization of nanoparticles. It is most likely driven by capillarity and aided by hydrogen bonding between nanoparticles and solvent molecules during freeze-drying. Due to the hydrogen bonding between OH groups on the nanoparticle surfaces and water molecules in the solvent, during the sublimation process, solvent molecules "pull" small nanoparticles with them, and help them organize themselves locally into a preliminary "loose" (i.e., wet) but relatively stable sheet structure. Further sublimation of water molecules can then exert strong forces on these sheets. Due to density fluctuations, the stress distribution is not uniform throughout the sheet and at some points the stress can be much higher than at others. Such non-uniform stresses can result in the formation of bumps, which are the prototypes of tube caps. Further stress release promotes the growth of bumps into the lower-energy end-capped tubes. Finally, the tubes can break from the "mother" sheets and leave behind holes in the sheets. The process for the formation of regular tube structures is quite repeatable when suitable experimental parameters are used. In addition, edges of the sheets may curl up to form irregular curved structures. The transition from sheet structure to tube structure appears to be the reason that the relative amounts of tubes and sheets change with time during freeze-drying. Any factor influencing the stress distribution could influence the formation of the resulting structures. For example, a disturbance in the very early stage of the tube growth may cause the early separation of a bump from the sheet and subsequent sphere formation due to energy minimization.

Water molecules, however, are not totally removed by the drying process. The remaining thin water layer hydrogen-bonds on both sides to surface hydroxyls on the neighboring nanoparticles and works as an adhesive force supporting the resulting tube or sheet structures. Thus, the interfacial structure between the neighboring nanoparticles of this arrangement would be: nanoparticle/surface-OH group/thin water layer/surface-OH group/nanoparticle.

The existence of such a thin water layer in these samples has been demonstrated by thermogravimetric analysis and Fourier-transform infrared spectroscopy, and this model can easily explain the observed sensitivity of the tube formation to the pH value of the suspension. The amount of the hydrogen-bonding formed influences the resulting structure by affecting the force exerted on the nanoparticles, thus affecting the preliminary, local spatial arrangement of nanoparticles and accordingly the stress distribution in the further sublimation process. Therefore, as the pH changes to relatively higher or lower values, the formation of the microtube structures becomes impossible. Nevertheless, many sheets still show partially curved structures near the edges. This nanoparticle-solvent-nanoparticle interaction mechanism is further supported by the following experiment: instead of distilled water, cyclohexane, which cannot form hydrogen bonds with the nanoparticles, was used as the solvent; no tubes were observed in this case.

Figure 3:
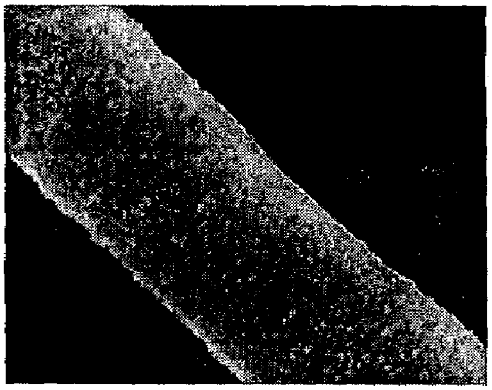
FIG. 3 is a FESEM image showing an individual $Al_2O_3$ microtube with its constituent nanoparticles.

Based on the above discussion, it is apparent that the formation of this tube structure is closely related to the large surface areas and surface hydroxyls on the nanoparticles. Thus, the process for this tube assembly should be generally applicable to any relatively equiaxed nanoparticles of sufficiently small size with hydrophilic surfaces. A preliminary result for the assembly of $Al_2O_3$ microtubes is shown in FIG. 3. It was also found that ZnO nanoparticles self-assembled in the same way. However, the surfaces of the ZnO tubes are much rougher, which may simply be due to the less equiaxed morphology of ZnO nanoparticles.

It should be noted that numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, or time, for example, from 1 to 90, preferably from 20 to 80, more preferably from 30 to 70, it is intended that values such as 15 to 85, 22 to 68, 43 to 51, 30 to 32 etc. are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

What is claimed is:

1. A process for producing microtubes from nanoparticles, said process comprising forming a dispersion of the nanoparticles in a liquid phase; and freeze-drying the dispersion to produce microtubes comprising an assembly of the nanoparticles;

wherein the nanoparticles comprise surface functionality for self-bonding and bonding with the liquid phase during freeze-drying.

2. A process for producing microtubes from nanoparticles having surface hydroxy functionality, said process comprising dispersing nanoparticles having surface functionality for self-bonding and bonding with the liquid phase during freeze-drying in a hydrogen-bonding liquid; and freeze-drying the dispersion to produce microtubes comprising an assembly of the nanoparticles;

wherein concentration of the nanoparticles in the hydrogen-bonding liquid ranges from 0.0025 to 0.0625 g/ml.

3. A process according to claim 2, wherein the nanoparticles comprise metal oxide.

4. A process according to claim 2, wherein the nanoparticles comprise titanium dioxide.

5. A process according to claim 2, wherein the nanoparticles comprise aluminum oxide.

6. A process according to claim 2, wherein the nanoparticles comprise zinc oxide.

7. A process according to claim 2, wherein the hydrogen-bonding liquid comprises water.

8. A process according to claim 7, wherein pH of the dispersion ranges from 1.8 to 2.8.

9. A process according to claim 7, wherein pH of the dispersion ranges from 1.9 to 2.7.

10. A process according to claim 7, wherein pH of the dispersion ranges from 2.0 to 2.6.

11. A process according to claim 7, wherein pH of the dispersion ranges from 2.1 to 2.5.

12. A process according to claim 7, wherein pH of the dispersion ranges from 2.2 to 2.4.

13. A process according to claim 2, wherein average particle size of the nanoparticles ranges from 10–30 nm.

14. A process according to claim 2, additionally comprising centrifuging the dispersion and freeze-drying a supernatant portion of the centrifuged dispersion.

15. A process for producing microtubes from nanoparticles having surface hydroxy functionality, said process comprising forming a dispersion consisting essentially of having surface functionality for self-bonding and bonding with the liquid phase during freeze-drying nanoparticles in a hydrogen-bonding liquid; and freeze-drying the dispersion to produce microtubes comprising an assembly of the nanoparticles;

wherein concentration of the nanoparticles in the liquid ranges from 0.0025 to 0.0625 g/ml.

16. A process according to claim 15, wherein the hydrogen-bonding liquid comprises water.

* * * * *

UNITED STATES PATENT AND TRADEMARK OFFICE
CERTIFICATE OF CORRECTION

PATENT NO. : 6,960,378 B1 Page 1 of 1
DATED : November 1, 2005
INVENTOR(S) : Siegel et al.

It is certified that error appears in the above-identified patent and that said Letters Patent is hereby corrected as shown below:

Column 9,
Line 11, insert the word -- nanoparticles -- after the word "of".

Signed and Sealed this

Twenty-seventh Day of December, 2005

JON W. DUDAS
*Director of the United States Patent and Trademark Office*